(12) United States Patent
Stein et al.

(10) Patent No.: US 12,167,873 B2
(45) Date of Patent: Dec. 17, 2024

(54) SPINAL FIXATION ASSEMBLY

(71) Applicant: Stryker European Operations Holdings LLC, Kalamazoo, MI (US)

(72) Inventors: Joshua Stein, Montvale, NJ (US); Steven F. Krause, Oakland, NJ (US); Anthony J. Wirtel, III, Malvern, PA (US); Charles L Bush, Jr., Wayne, NJ (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 217 days.

(21) Appl. No.: 17/842,160

(22) Filed: Jun. 16, 2022

(65) Prior Publication Data

US 2022/0313322 A1    Oct. 6, 2022

Related U.S. Application Data

(63) Continuation of application No. 16/870,273, filed on May 8, 2020, now Pat. No. 11,389,208, which is a continuation of application No. 15/649,903, filed on Jul. 14, 2017, now Pat. No. 10,687,859.

(60) Provisional application No. 62/362,690, filed on Jul. 15, 2016.

(51) Int. Cl.
*A61B 17/70* (2006.01)
*A61B 17/00* (2006.01)

(52) U.S. Cl.
CPC ...... *A61B 17/7041* (2013.01); *A61B 17/7011* (2013.01); *A61B 17/7014* (2013.01); *A61B 17/7025* (2013.01); *A61B 17/7035* (2013.01); *A61B 2017/00991* (2013.01)

(58) Field of Classification Search
CPC ............ A61B 17/7011; A61B 17/7014; A61B 17/7041; A61B 17/7043; A61B 17/7049; A61B 17/705
USPC ........................................ 606/250, 260, 278
See application file for complete search history.

(56) References Cited

U.S. PATENT DOCUMENTS

| 5,133,715 | A | * | 7/1992 | Lenzo | A61B 17/88 606/53 |
|---|---|---|---|---|---|
| 5,810,815 | A | | 9/1998 | Morales | |
| 6,187,005 | B1 | | 2/2001 | Brace et al. | |
| 6,280,445 | B1 | | 8/2001 | Morrison et al. | |

(Continued)

FOREIGN PATENT DOCUMENTS

| DE | 102012202749 A1 | 8/2013 |
|---|---|---|
| JP | 2007167658 A | 7/2007 |
| JP | 2012522584 A | 9/2012 |

OTHER PUBLICATIONS

Partial European Search Report for EP 17 18 1196 completed Dec. 8, 2017.

(Continued)

*Primary Examiner* — Eduardo C Robert
*Assistant Examiner* — Christina Negrellirodriguez
(74) *Attorney, Agent, or Firm* — Lerner David LLP

(57) ABSTRACT

Disclosed herein are a spinal fixation assembly and method to provide adequate rigidity and support for a vertebral column without requiring additional pedicle screws and spinal rods. The spinal fixation assembly includes a spinal rod loop with multiple sides configured to be attached to a vertebral body with two or more pedicle screws. Each pedicle screw is adapted to fit at various locations along the spinal rod loop.

10 Claims, 13 Drawing Sheets

(56) References Cited

U.S. PATENT DOCUMENTS

| | | | |
|---|---|---|---|
| 6,485,491 B1 | 11/2002 | Farris et al. | |
| 7,699,874 B2* | 4/2010 | Young | A61B 17/705 606/280 |
| 7,976,567 B2 | 7/2011 | Null et al. | |
| 8,016,861 B2 | 9/2011 | Mitchell et al. | |
| 8,226,695 B2* | 7/2012 | Moore | A61B 17/7044 606/286 |
| 8,337,532 B1 | 12/2012 | McLean et al. | |
| 8,523,906 B2 | 9/2013 | McLean et al. | |
| 8,758,411 B1 | 6/2014 | Rayon et al. | |
| 8,882,803 B2* | 11/2014 | Lott | A61B 17/705 606/264 |
| 8,906,067 B2 | 12/2014 | Traynelis et al. | |
| 8,998,956 B2* | 4/2015 | George | A61B 17/7001 606/250 |
| 8,998,961 B1* | 4/2015 | Ziemek | A61B 17/705 606/260 |
| 9,247,964 B1 | 2/2016 | Shoshtaev | |
| 2005/0010215 A1* | 1/2005 | Delecrin | A61B 17/7011 606/264 |
| 2005/0277920 A1* | 12/2005 | Slivka | A61B 17/7044 606/279 |
| 2007/0225708 A1 | 9/2007 | Biedermann et al. | |
| 2007/0250061 A1 | 10/2007 | Chin et al. | |
| 2007/0270836 A1 | 11/2007 | Bruneau et al. | |
| 2008/0021456 A1* | 1/2008 | Gupta | A61B 17/7049 606/250 |
| 2009/0036929 A1 | 2/2009 | Reglos et al. | |
| 2011/0004251 A1 | 1/2011 | Sweeney et al. | |
| 2011/0046675 A1 | 2/2011 | Barrus et al. | |
| 2012/0089189 A1 | 4/2012 | Binder et al. | |
| 2013/0006306 A1 | 1/2013 | Saidha et al. | |
| 2014/0135840 A1* | 5/2014 | McClintock | A61B 17/7011 606/265 |
| 2014/0249584 A1* | 9/2014 | Seex | A61B 17/7043 606/279 |
| 2014/0277156 A1 | 9/2014 | Hammer | |
| 2015/0223844 A1 | 8/2015 | Leff et al. | |
| 2015/0335361 A1* | 11/2015 | Henderson, Sr. | A61B 17/7055 606/280 |
| 2016/0058478 A1 | 3/2016 | Agarwal et al. | |
| 2017/0238969 A1* | 8/2017 | Sylvia | A61B 17/7032 |
| 2017/0265901 A1 | 9/2017 | Hawkins et al. | |
| 2018/0132905 A1 | 5/2018 | Le Couedic et al. | |
| 2018/0228516 A1 | 8/2018 | Armstrong et al. | |
| 2018/0228518 A1 | 8/2018 | Carruth et al. | |

OTHER PUBLICATIONS

European Search Report for EP 17174582 completed on Nov. 2, 2017.

* cited by examiner

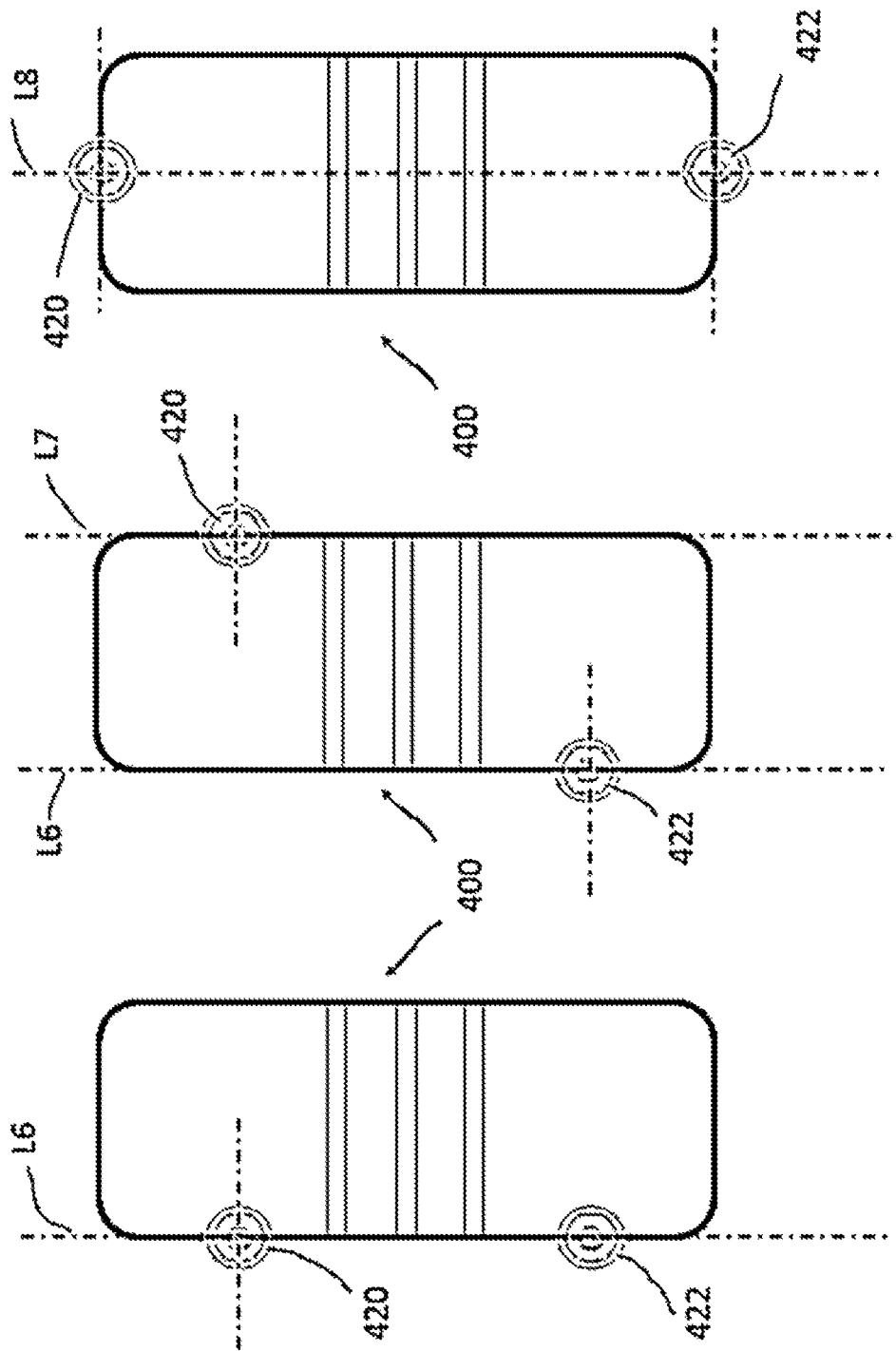

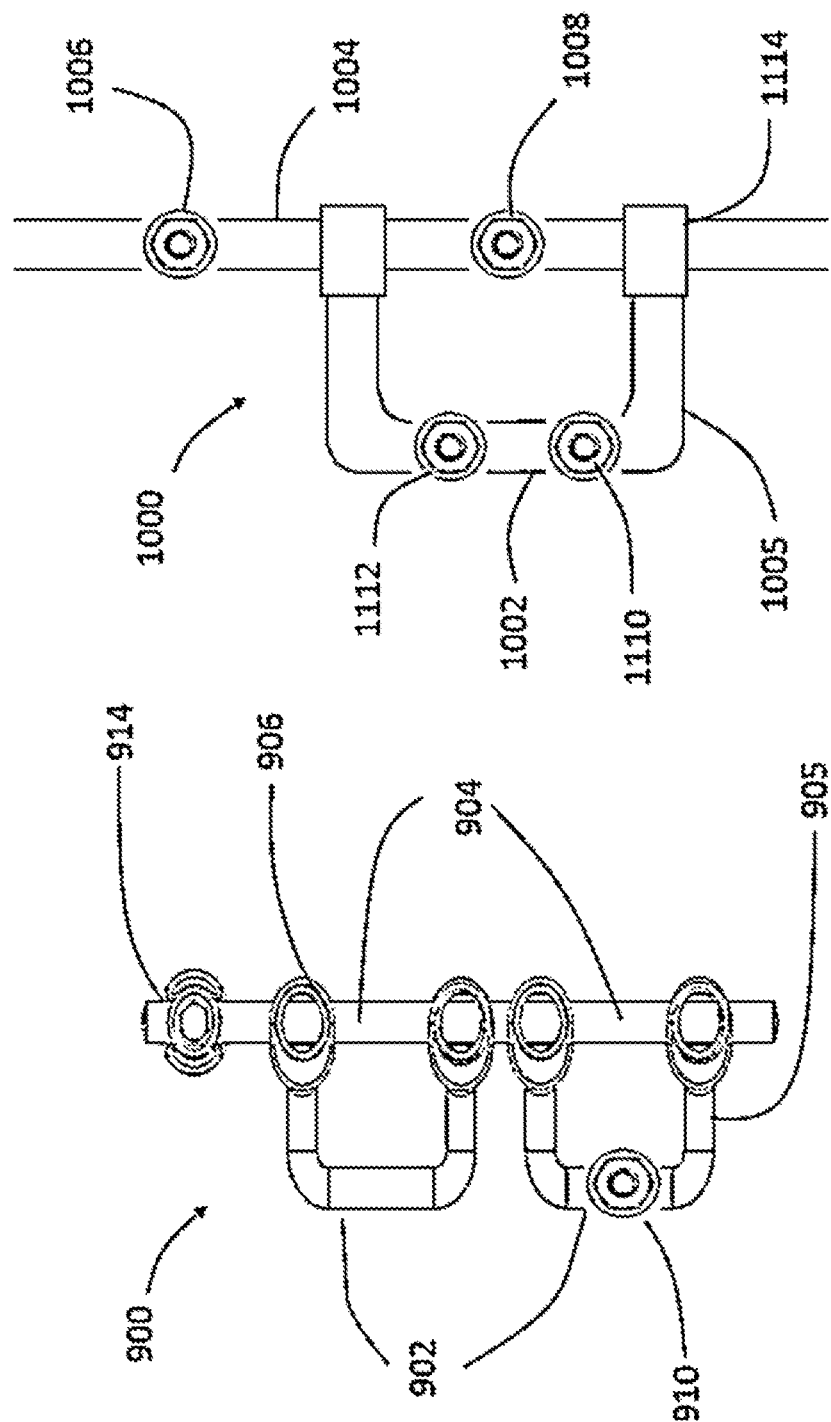

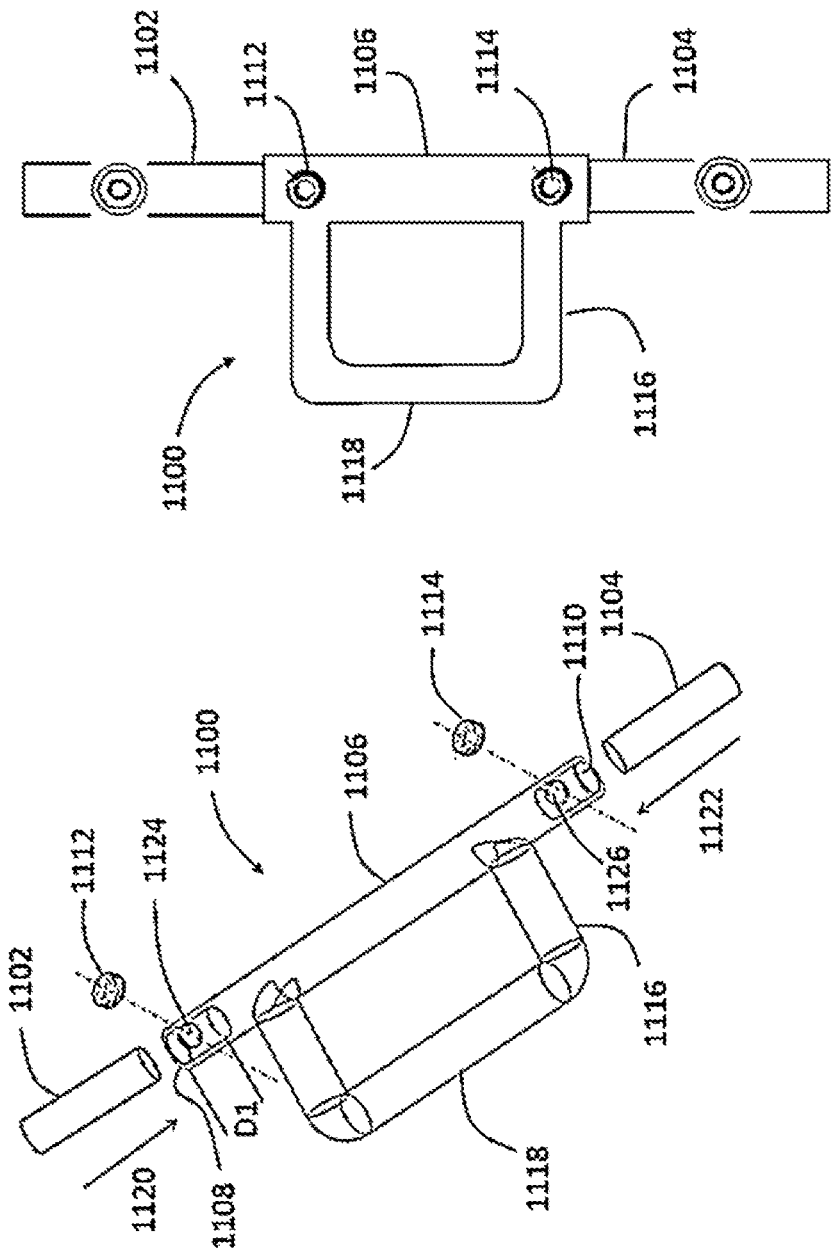

SPINAL FIXATION ASSEMBLY

CROSS-REFERENCE TO RELATED APPLICATION

This application is a continuation of U.S. application Ser. No. 16/870,273, filed on May 8, 2020, which is a continuation of U.S. application Ser. No. 15/649,903, filed on Jul. 14, 2017, which claims the benefit of the filing date of U.S. Provisional Patent Application No. 62/362,690, filed on Jul. 15, 2016, the disclosures of which are hereby incorporated herein by reference.

BACKGROUND OF THE INVENTION

The present invention relates to an assembly and a method for spinal fixation, and in particular relates to a spinal rod and a method for spinal fixation configured to reduce the use of bone penetrating connections and/or additional fixture devices.

Spinal rods are routinely used in spinal fusion procedures to treat different spinal disorders, such as scoliosis, degenerative disc disease, disc herniation, spinal stenosis, or other abnormalities. Typically, such procedures involve properly aligning two or more vertebrae and permanently fusing them together through the use of two or more pedicle screws attached by the spinal rods. This construct stabilizes the spine until fusion occurs.

Spinal rod fracture is the most common type of fixation device failure in spinal fusion procedures. Particularly in procedures such as corrective osteotomy and long-segment spinal fusion, the risk of spinal rod failure can be significant. Spinal rod fractures occur because the implanted spinal rod is unable to sustain the load long enough to allow the vertebrae to fuse together. Rod failure generally does not occur over a single overloading event (shock loading), but instead occurs due to fatigue over time. To prevent spinal rod failure, multiple spinal rods across the same vertebral bodies may be required. For example, when a single spinal rod is unable to provide the necessary support, multiple rods across the same vertebral bodies may be connected with additional bone anchoring pedicle screws to provide additional rigidity.

A "quad rod" technique uses four rods instead of two rods across the vertebrae. A second rod is added to the main rod on each side of the spinous process and connected by rod-to-rod connectors to increase overall rigidity of the fixation assembly. However, the quad rod technique requires multiple rod-to-rod connectors to connect the first and second rod to each other, which further complicates the spinal fusion surgery by adding additional surgery time and effort to locate and place connectors in narrow regions between screws and rods. Furthermore, the rod-to-rod connector connections at the spinal rod represent the weakest point of the spinal rod, and hence the area most susceptible to structural failure. The greater amount of connection points lead to more potential rod failure points. Additional rod interfaces, and rod-to-rod connectors may exacerbate the risk of stress related failure.

Therefore, there exists a need to provide a spinal fixation assembly and method that provides rigidity without requiring additional fixture devices.

BRIEF SUMMARY OF THE INVENTION

Disclosed herein are spinal fixation assemblies and methods for spinal fixation configured to reduce the use of bone penetrating connections and/or additional fixture devices In a first aspect of the present invention, a spinal fixation assembly is provided. The spinal fixation assembly may include a first pedicle screw with a first channel and a second pedicle screw with a second channel. The spinal fixation assembly may have one or more loops. Each loop may have a loop thickness and may be defined by a spinal rod thickness. The first and second channels may be at least as wide as the spinal rod thickness and narrower than the loop thickness.

In accordance with the first aspect, the first and second pedicle screw may each include a bone portion and a tulip polyaxially moveable with respect to the bone screw portion. The loop may be a closed loop. The loop may be lemniscate shaped. The loop may include variable dimension. The loop may also have telescopic portions which may include a ladder portion for reinforcing the loop.

In other aspects, the loop may include first and second sides. The first side may engage with the first pedicle screw and the second side may engage with the second pedicle screw.

In a second aspect of the present invention, a spinal rod assembly is provided. The spinal rod assembly may include a spinal rod, a spinal rod connector, a first pedicle screw, a second pedicle screw and a third pedicle screw. The spinal rod connector may have connector rod which may have a coupling mechanism adapted to fit the spinal rod. The first and second pedicle screws may attach the spinal rod to a vertebral body. The coupling mechanism of the spinal rod connector may connect the spinal rod to the spinal rod connector. The third pedicle screw may connect the connector rod to the vertebral body.

In accordance with the second aspect, the spinal rod may be a loop which may include one or more sides. The first and second pedicle screws may attach to one loop side.

In a third aspect of the present invention, a spinal rod assembly is provided. The spinal rod assembly may include a spinal rod, a spinal rod reinforcer, a first pedicle screw and a second pedicle screw. The spinal rod reinforcer may have one or more arms. Each arm may have a coupling mechanism adapted to fit the spinal rod. The first and second pedicle screw may attach the spinal rod to a vertebral body. The coupling mechanism of the spinal rod reinforcer may be attached to the spinal rod.

In accordance with the third aspect, the spinal rod loop may have one or more sides. The first and second pedicle screws may be attached to one loop side. One or more pedicle screws may attach the spinal rod reinforcer to the vertebral body.

In other aspects, at least two arms of the spinal rod reinforcer may be attached to opposite ends of a central portion of the spinal rod reinforcer. The spinal rod reinforcer may be substantially C-shaped. The central portion of the spinal rod reinforcer may be substantially parallel to the spinal rod. The spinal rod reinforcer may be monolithic.

In a fourth aspect of the present invention, a spinal rod assembly is provided. The spinal rod assembly may include a first spinal rod, a second spinal rod, and a spinal rod connector. The spinal rod connector may have a reinforcer component. The reinforcer component may be attached to the spinal rod connector by two arms. Two openings at opposite ends of the spinal rod connector may be provided to receive the first and second spinal rods. A length of the openings may be varied to adjust the placement of the spinal rods relative to the spinal rod connector. Set screws may be used to secure spinal rods to spinal rod connector. The spinal rod connector with the reinforcer component may be monolithic.

A fifth aspect of the present invention is a method of securing a spinal fixation assembly having two pedicle screws and a spinal rod loop. A method in accordance with this aspect of the invention may include the steps of inserting a first pedicle screw on a first vertebrae and a second pedicle screw on a second vertebrae, connecting the first pedicle screw to a loop side of the spinal rod loop on the first vertebrae, and connecting the second pedicle screw to the same loop side of the spinal rod loop on the second vertebrae. The second pedicle screw may be connected to a second loop side of the spinal rod loop.

A sixth aspect of the present invention is a method of performing a quad rod procedure to attach a spinal rod reinforcer to a spinal rod. A method in accordance with this aspect of the invention may include the steps of connecting a first arm of a spinal rod reinforcer to a first location on the spinal rod, connecting a second arm of the spinal rod reinforcer to a second location on the spinal rod, inserting a pedicle screw on a vertebrae medially or laterally adjacent to the spinal rod, and connecting a central portion of a spinal rod reinforcer to the pedicle screw. The second pedicle screw may be inserted between the first and second location on the spinal rod.

BRIEF DESCRIPTION OF THE DRAWINGS

A more complete appreciation of the subject matter of the present invention and the various advantages thereof can be realized by reference to the following detailed description, in which reference is made to the following accompanying drawings:

FIG. 7A is a top view of the spinal rod loop and pedicle screw assembly of FIG. 5 showing a first arrangement among the loop and pedicle screws.

FIG. 7B is a top view of the spinal rod loop and pedicle screw assembly of FIG. 5 showing a second arrangement among the loop and pedicle screws.

FIG. 7C is a top view of the spinal rod loop and pedicle screw assembly of FIG. 5 showing a third arrangement among the loop and pedicle screws.

FIG. 13A is a top view of a spinal rod reinforcer according to another embodiment of the present invention.

FIG. 13B is a top view of a spinal rod reinforcer according to yet another embodiment of the present invention.

FIG. 14A is a perspective view of a spinal rod connector according to one embodiment of the present invention.

FIG. 14B is a top view of the spinal rod connector of FIG. 14A connected to a first and a second spinal rod.

DETAILED DESCRIPTION

Figure 1:
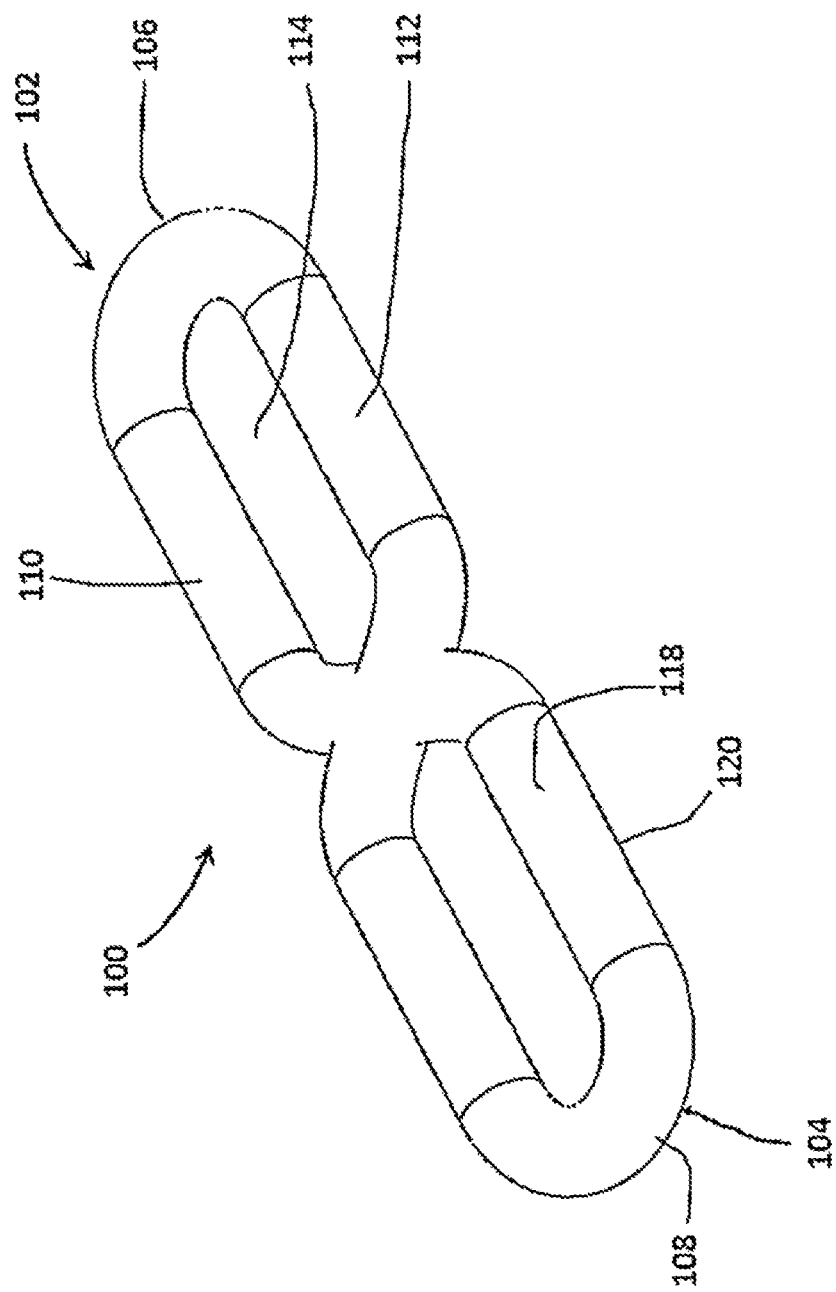
FIG. 1 is a perspective view of a spinal rod loop according to one embodiment of the present invention.

Referring to FIG. 1, shows a perspective view of an embodiment of a spinal rod loop 100 according to the present invention. Spinal rod loop 100 comprises a first elliptical-shaped member 102 and an adjoining second elliptical-shaped member 104. The loop has an upper superior side 106, a lower inferior side 108, a medial side 110, and a lateral side 112 enclosing an inner aperture 114. Spinal rod loop 100 also has an anterior surface 118 facing a vertebra, and an opposing posterior surface 120 facing away from the vertebra. The lemniscate-shaped spinal rod of this embodiment provides a significant increase in rigidity over a traditional spinal rod because the elliptical-shaped members of this spinal rod loop allow for improved stress distribution. Consequently, the increased stiffness of this spinal rod will minimize deflection or micromotion as compared to a single rod, which has been known to increase chances of fusion.

Figure 2:
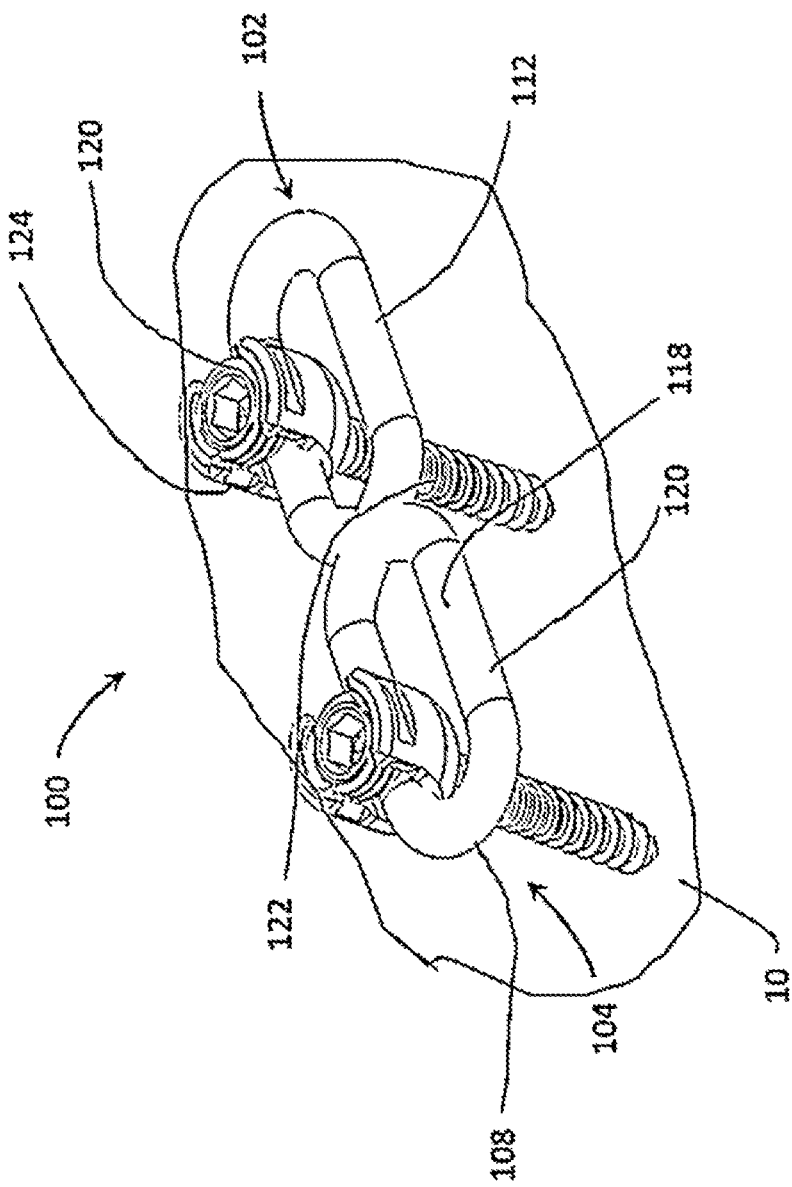
FIG. 2 is a perspective view of the spinal rod loop of FIG. 1 and pedicle screw assembly connected to a vertebral column.

FIG. 2 shows a perspective view of spinal rod loop 100 connected to two adjacent vertebral segments of a vertebral column 10. Medial side 110 of first elliptical-shaped member 102 is connected to a first pedicle screw 120, and medial side 110 of second elliptical-shaped member 104 is connected to a second pedicle screw 122. As shown, pedicle screw channel 124 is slightly wider than the thickness of medial side 110 of spinal rod loop 100, so that the pedicle screw channel is adapted to couple with one side of the spinal rod loop. In the embodiments shown, the thickness or diameter of the spinal rod loop 100 is 3.5-6.35 mm and the length is at least approximately 30 mm. In other embodiments, the rod may extend over multiple spinal levels and therefore will have multiple elliptical-shaped members. In this design, the length could be as much as 860 mm. In still further embodiments, the individual elliptical-shaped members may not necessarily be of the same length. The width of the spinal rod loop ranges between approximately 10-100 mm. The dimensions of the spinal rod loop 100 are based on the levels of the vertebra that is being fixed, and therefore can widely vary.

Figure 3:
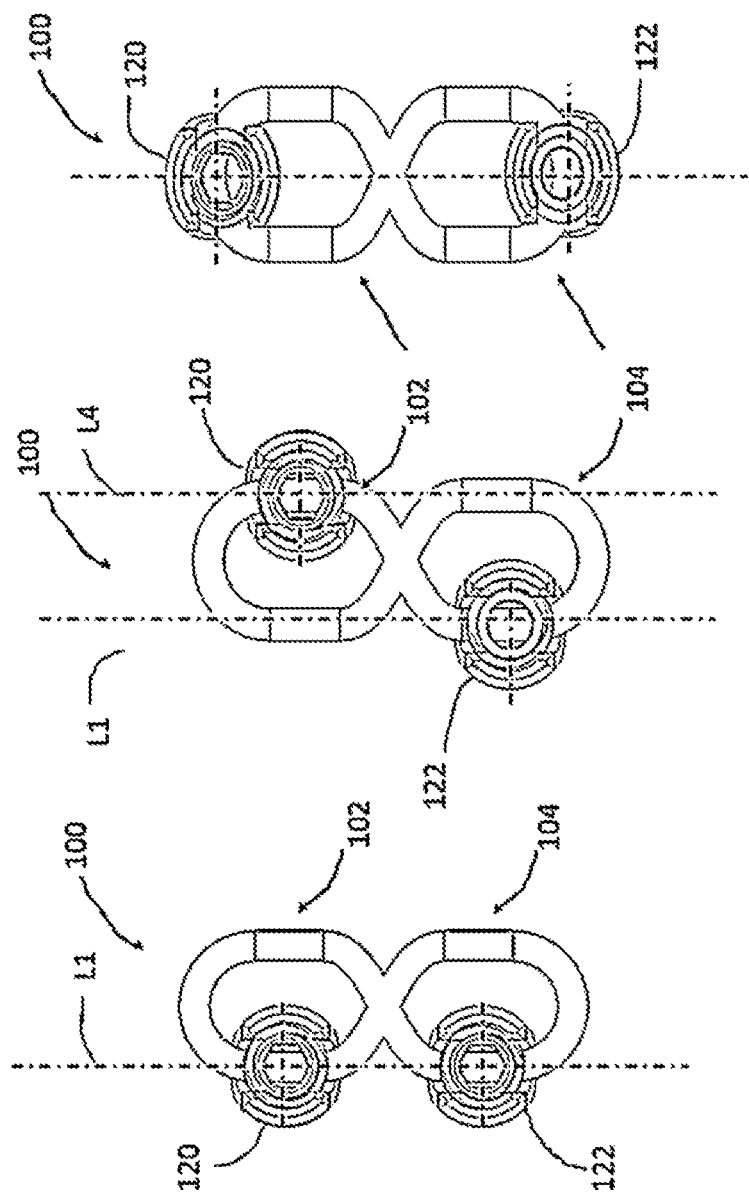
FIG. 3A is a top view of the spinal rod loop and pedicle screw assembly of FIG. 1 showing a first arrangement among the loop and pedicle screws.
FIG. 3B is a top view of the spinal rod loop and pedicle screw assembly of FIG. 1 showing a second arrangement among the loop and pedicle screws.
FIG. 3C is a top view of the spinal rod loop and pedicle screw assembly of FIG. 1 showing a third arrangement among the loop and pedicle screws.

The sides of spinal rod loop 100 provide multiple coupling locations for the pedicle screws. FIG. 3A shows a first arrangement in which first pedicle screw 120 and second pedicle screw 122 are coupled to medial side 110 of each elliptical-shaped member respectively. As shown, the medial sides of both elliptical-shaped members are along a common longitudinal axis L1 as both elliptical-shaped members are the same size in this embodiment. In other embodiments, adjoining elliptical-shaped members may not be of similar size or shape, and consequently the medial sides of these members may not lie on a common longitudinal axis. In still other embodiments, the length of the individual members may vary but all members may have the same width, and thereby the medial sides of these members may lie on a common longitudinal axis. FIG. 3B shows a second arrangement of the pedicle screws where first pedicle screw 120 is coupled with medial side 110 of first elliptical-shaped member 102, and second pedicle screw 122 is coupled with lateral side 112 of second elliptical-shaped member 104. The pedicle screws in this arrangement are situated along two different longitudinal axes L1 and L4. FIG. 3C shows a third arrangement of the pedicle screws where first pedicle screw 120 is coupled with upper superior side 106, and second pedicle screw 122 is coupled with lower inferior side 108. Thus, as shown in FIGS. 3A-C, the multiple sides of spinal loop rod 100 provide multiple locations for pedicle screw connections, thereby allowing increased flexibility to properly locate and attach pedicle screws in different arrangements. Furthermore, spinal rod loop 100 provide the rigidity and support of multiple single rods but only requires two pedicle screws to properly secure the spinal rod loop to the vertebral columns, thereby reducing the number of bone anchoring penetrations required in the assembly.

Elliptical-shaped members 102, 104 shown in this first embodiment are of the same size and shape, however, other embodiments may have members of different sizes and shapes to vary the rigidity and connection locations of the pedicle screws. For instance, it is contemplated to have rectangular-shaped portions forming loop 100 or the like. Furthermore, the members may be differently sized so that one member is larger than the other in length and or width. In still other embodiments, there may be more than two members in the spinal rod loop. A number of elliptical-shaped members can be connected or rod loops may be connected in series as well.

In a method according to a further aspect of the present invention, spinal rod loop 100 is utilized with two pedicle screws (120,122) to fuse adjacent vertebral bodies. Although loop 100 may be utilized in many types of surgeries, it is designed for use in situations where multiple spinal rods may have otherwise been employed, for instance, spinal osteotomy procedures like pedicle subtraction osteotomy. Whatever the procedure, subsequent to implantation of two or more pedicle screws loop 100 is placed in engagement with the pedicle screws, much like in a typical pedicle screw fusion procedure. However, the design of loop 100 preferably provides a fixation with a strength approaching or even exceeding that of a two rod construct provided in certain situations, as noted above. The spinal rod may even span contralaterally weaving between a spinous processes (not shown).

Figure 4:
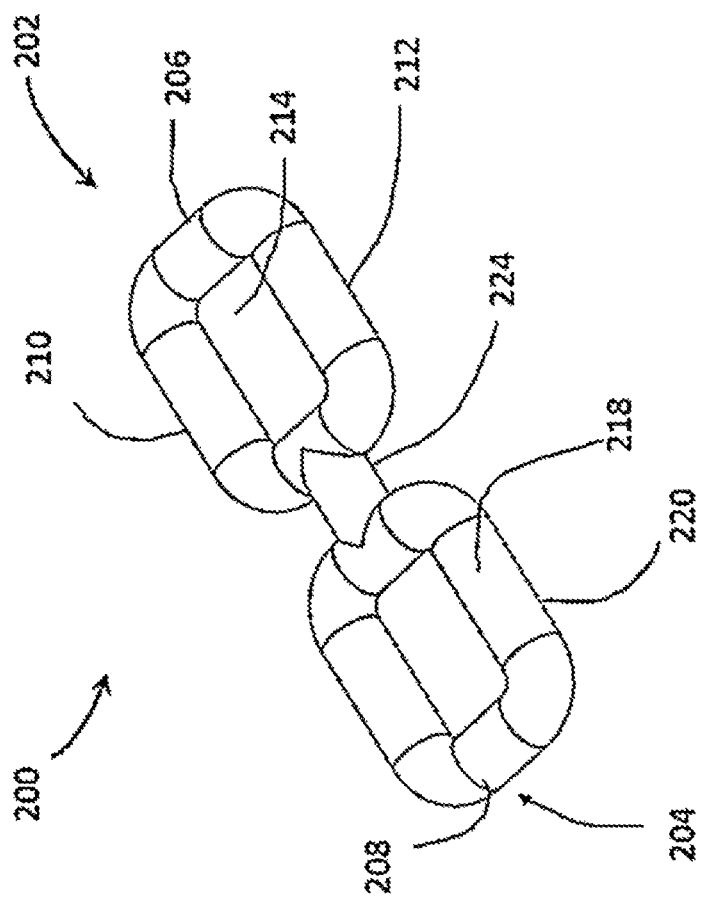
FIG. 4 is a perspective view of a spinal rod loop according to another embodiment of the present invention.

FIG. 4 shows a perspective view of another embodiment of a spinal rod loop 200. Spinal rod loop 200 is similar to spinal rod loop 100, and therefore like elements are referred to with similar reference numeral within the 200-series. For instance, spinal rod loop 200 includes first and second elliptical-shaped members 202, 204. However, where those members are directly attached to another in spinal rod loop 100, spinal rod loop 200 of this embodiment includes an additional connector element 224 connecting the members. Connector element 224 may have a different cross section, i.e., thicker or thinner than loop 200 thickness. As shown in FIGS. 3A-C of spinal rod loop 100, pedicle screw locations and arrangements can similarly be varied for spinal rod loop 200.

Figure 5:
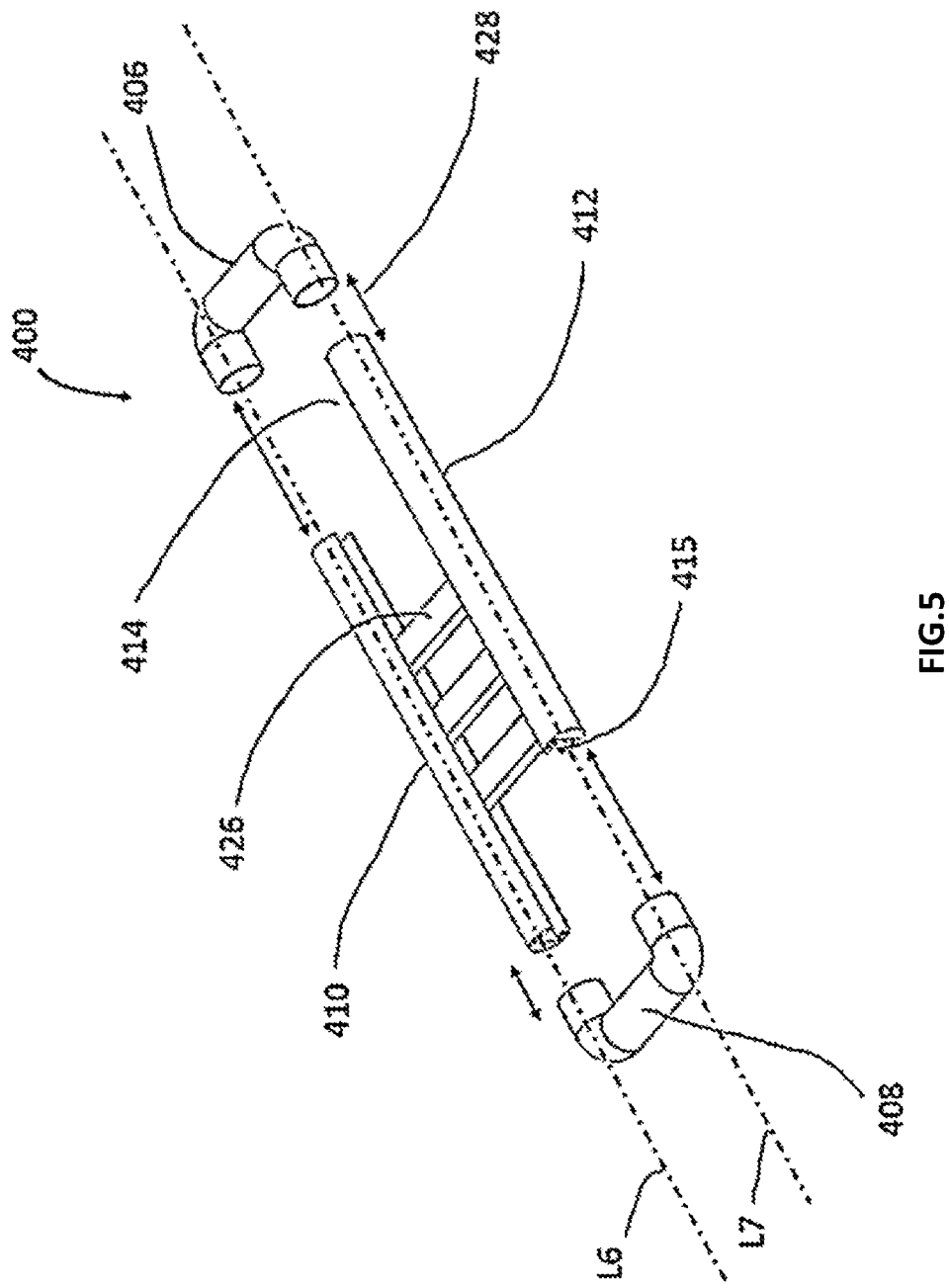
FIG. 5 is an exploded view of a spinal rod loop of yet another embodiment of the present invention.

FIG. 5 shows an exploded view of yet another embodiment of a spinal rod loop 400. The spinal rod loop according to this embodiment is a closed rectangular loop having an upper superior side 406, a lower inferior side 408, a medial side 410, and a lateral side 412 enclosing an inner aperture 414. Spinal rod loop 400 also has an anterior surface 418 facing a vertebra, and an opposing posterior surface 420 facing away from the vertebra. Three cross beams 426 span the width between medial side 410 and lateral side 412 reinforcing spinal rod loop 400. Medial side 410 and lateral side 412 include telescopic members 428 that can be adjusted along longitudinal axes L6 and L7, respectively, to readily vary the length of the spinal rod loop. Telescopic members 428 are slidably engaged with one another and are locked in place with the superior and inferior side of spinal rod loop 400 by tightening the pedicle screws. Medial side 410 and lateral side 412 have a slot 415 adapted to receive cross beams 426. Cross beams 426 can be moved along slot 415 and locked into desired position. The telescopic mechanism of spinal rod loop 400 also allows for varying the rigidity of the spinal rod by adjusting the length. The spinal rod loop provides more rigid support when the sliding telescopic members are retracted, and less rigid support when the telescopic members are extended. In other embodiments, ends 406 and 408 may be welded to the medial and lateral sides. While three cross beams are shown in this embodiment, other embodiments may have more or less than three cross beams.

Figure 6:
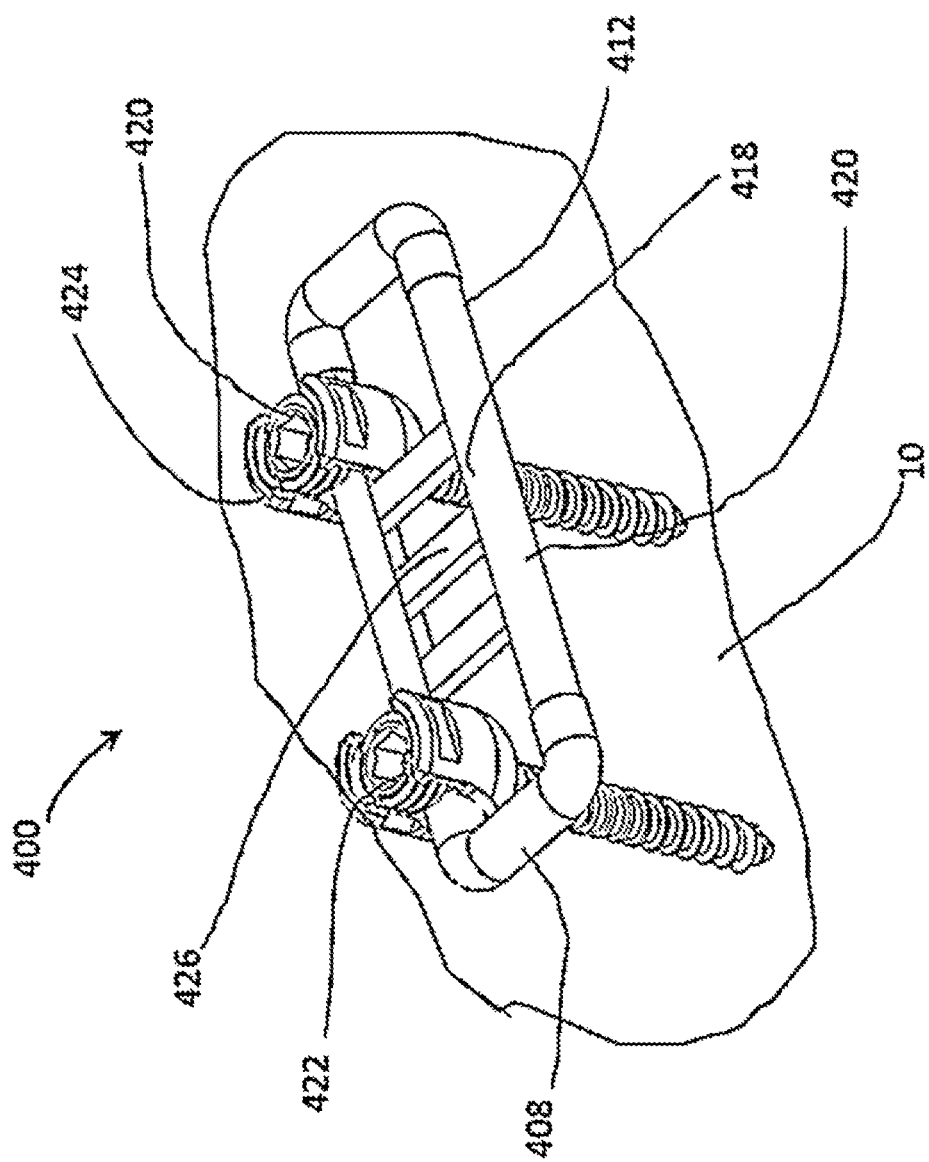
FIG. 6 is a perspective view of the spinal rod loop of FIG. 5 and pedicle screw assembly connected to a vertebral column.

FIG. 6 shows a perspective view of spinal rod loop 400 connected to two adjacent vertebral segments of a vertebral column 10. A first pedicle screw 420 and a second pedicle screw 422 are connected to medial side 410 of spinal rod loop 400. As shown, pedicle screw channel 424 is slightly wider than the thickness of medial side 410 of spinal rod loop 400, so that the pedicle screw channel is adapted to couple with one side of the spinal rod loop. Additionally, cross beams 426 are adjustable within slot 415 to allow for spinal rod loop 400 to fit within pedicle screw channel 424 and to avoid interfering with pedicle screws 420 and 422.

Similar to spinal rod loop 100, the sides of spinal rod loop 400 provide multiple coupling locations for the pedicle screws. FIG. 7A shows a first arrangement in which first pedicle screw 420 and second pedicle screw 422 are coupled to medial side 410. In this arrangement, the pedicle screws lie along a common longitudinal axis L6. FIG. 7B shows a second arrangement of the pedicle screws where first pedicle screw 420 is coupled with lateral side 412, and second pedicle screw 422 is coupled with the opposite medial side 410 of spinal rod loop 400. The pedicle screws in this arrangement are on two different longitudinal axes L6 and L7. FIG. 7C shows a third arrangement of the pedicle screws where first pedicle screw 420 is coupled with upper superior side 406 and second pedicle screw 422 is coupled with lower inferior side 408 of spinal rod loop 400. Thus, as illustrated in FIGS. 7A-C, the multiple sides of spinal loop rod 400 provide multiple locations for pedicle screw connections, thereby allowing increased flexibility to properly locate and attach pedicle screws. Furthermore, the multiple sides of spinal rod loop 400 provide the rigidity and support of multiple single rods but only require two pedicle screws to properly secure the spinal rod loop to the vertebral column, thereby reducing the number of bone anchoring penetrations required in the assembly. All spinal rod loop embodiments disclosed herein may be preoperatively or operatively bent to conform to pedicle screw insertion locations and the required rod placement on the spine. Spinal rod loops disclosed herein may be linked to each other with the rod-to-rod connectors disclosed in U.S. patent application Ser. No. 15/606,279, the disclosure of which is hereby incorporated by reference herein.

Figure 8:
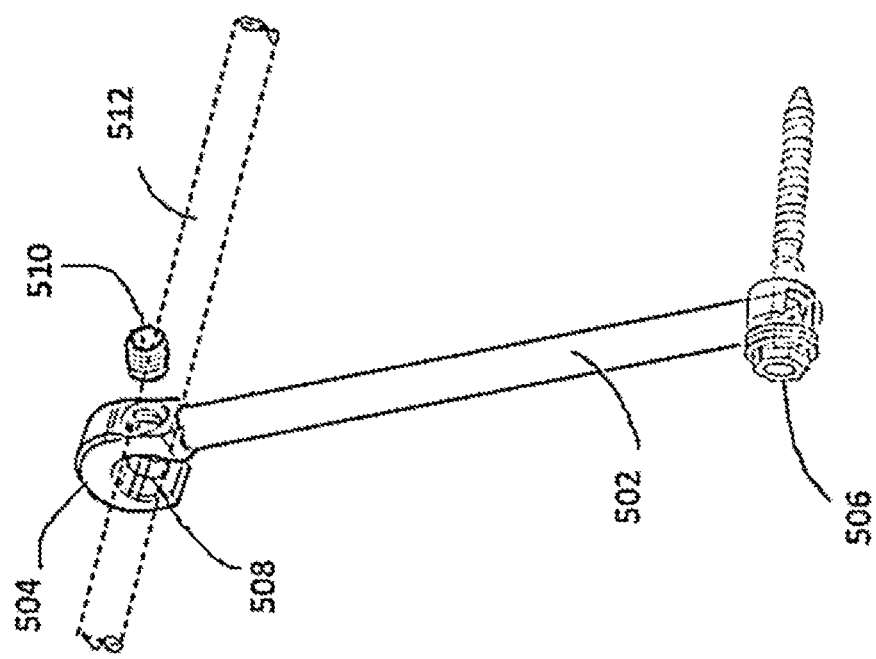
FIG. 8 is a perspective view of a spinal rod connector with a first coupling mechanism according to one embodiment of the present invention.

FIG. 8 is a perspective view of a spinal rod connector 500 according to a first embodiment. Spinal rod connector 500 includes a connector rod 502 with a coupling mechanism 504 on one end and a pedicle screw 506 on the opposite end. Coupling mechanism 504 has a channel 508 adapted to couple with a spinal rod 512. A set screw 510 secures the coupling mechanism 504 to spinal rod 512. Spinal rod connectors according to this embodiment may generally range from 10 mm to 100 mm in length with a thickness (diameter) of about 3.5 mm to 6.35 mm. Of course, as with other embodiments according to the present invention, these dimensions may vary widely depending upon the specific application.

Figure 9A:
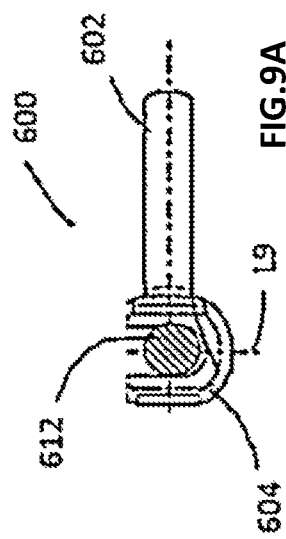
FIG. 9A is a side view of a spinal rod connector according to another embodiment of the present invention.
Figure 9B:
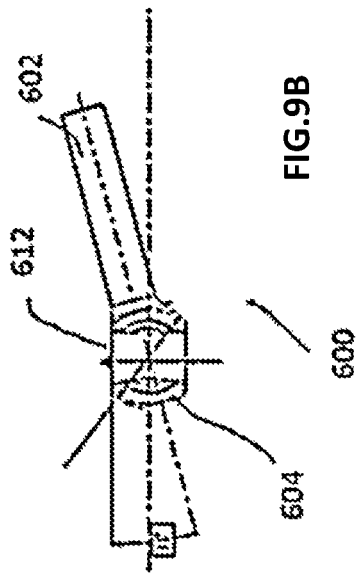
FIG. 9B is a top view of the spinal rod connector of FIG. 9A

FIGS. 9A and 9B show a spinal rod connector 600 with a second coupling mechanism 604. In this embodiment, a connector rod 602 attached to coupling mechanism 604 can rotate about a longitudinal axis L9. This rotation allows connector rod 602 to be readily adjusted to align and connect to a spinal rod 612.

Figure 10:
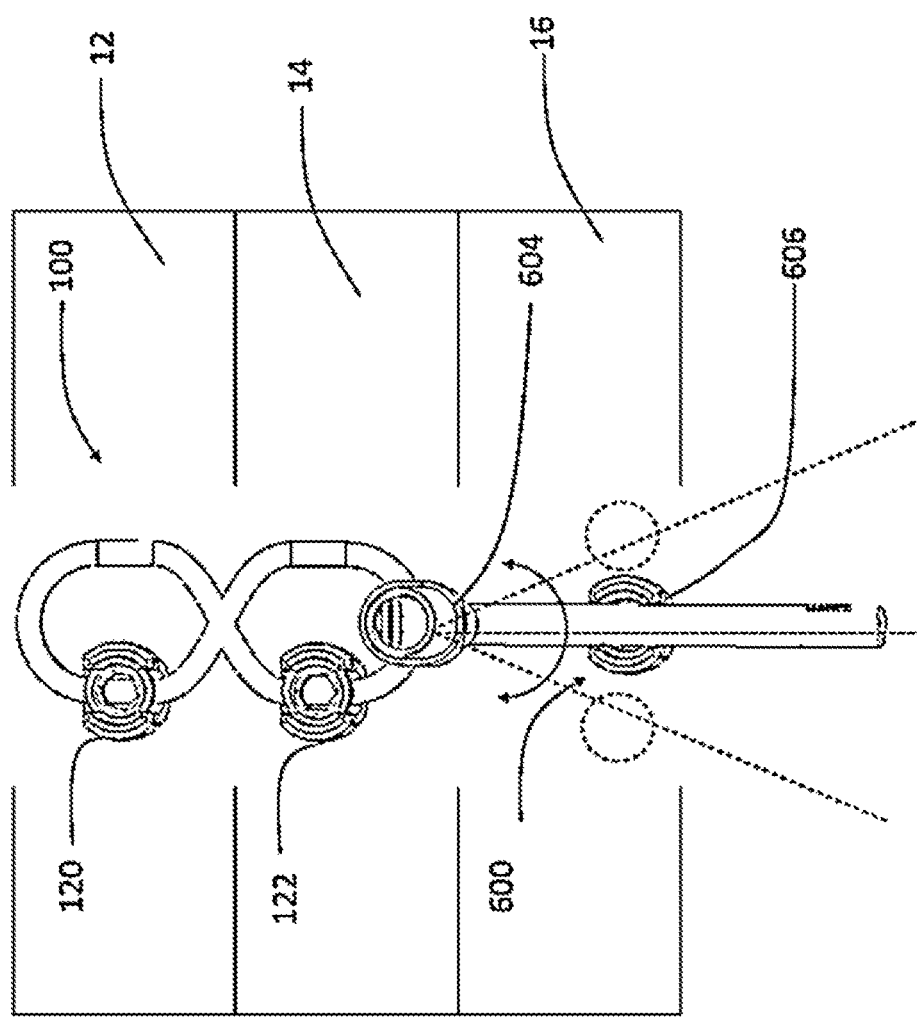
FIG. 10 is a top view of the spinal connector of FIG. 9A connected to the spinal rod loop of FIG. 1.

FIG. 10 shows a top view of spinal rod connector 600 of FIG. 9A connected to spinal rod loop 100 of FIG. 1. Spinal rod loop 100 connects a first vertebra 12 (via pedicle screw 120) to a second adjoining vertebra 14 (via pedicle screw 122). As shown, coupling mechanism 604 of spinal rod connector 600 is attached to lower inferior side 108 of second elliptical-shaped member 104. Coupling mechanism 604 allows for 180 degrees of rotation of spinal rod connector 600. The combined length of spinal rod connector 600 and spinal rod loop 100 shown in this specific embodiment may range from 45 mm to 860 mm. Spinal rod connector thicknesses (diameter) may range from 3.5 mm to 6.35 mm. In other embodiments, the coupling mechanism may be attached to other sides of the first or second elliptical member. In any event, because the opposite end of spinal rod connector 600 is anchored to a third vertebra 16 (via a pedicle screw 606), the assembly allows three vertebrae to be fused. Connector rod 602 can be rotated as shown in FIG. 9B to enable precise positioning of the pedicle screw insertion. This can be of concern especially if the third vertebra 16 is a sacral bone.

In a method according to a further aspect of the present invention, spinal rod connector 600 is used in conjunction with spinal rod loop 100 to fuse a third vertebra using only one pedicle screw 606. Spinal rod loop 100 is connected to first and second vertebra 14, 16 by a method like that described in paragraph [0029]. One end of the spinal rod connector is then connected to spinal rod 100 by attaching coupling mechanism 604, and the other end is connected to pedicle screw 606 to complete the assembly. Of course, it is contemplated to utilize connector 600 in connection with any of the loops disclosed herein as well as in connection with standard spinal rods.

Figure 11:
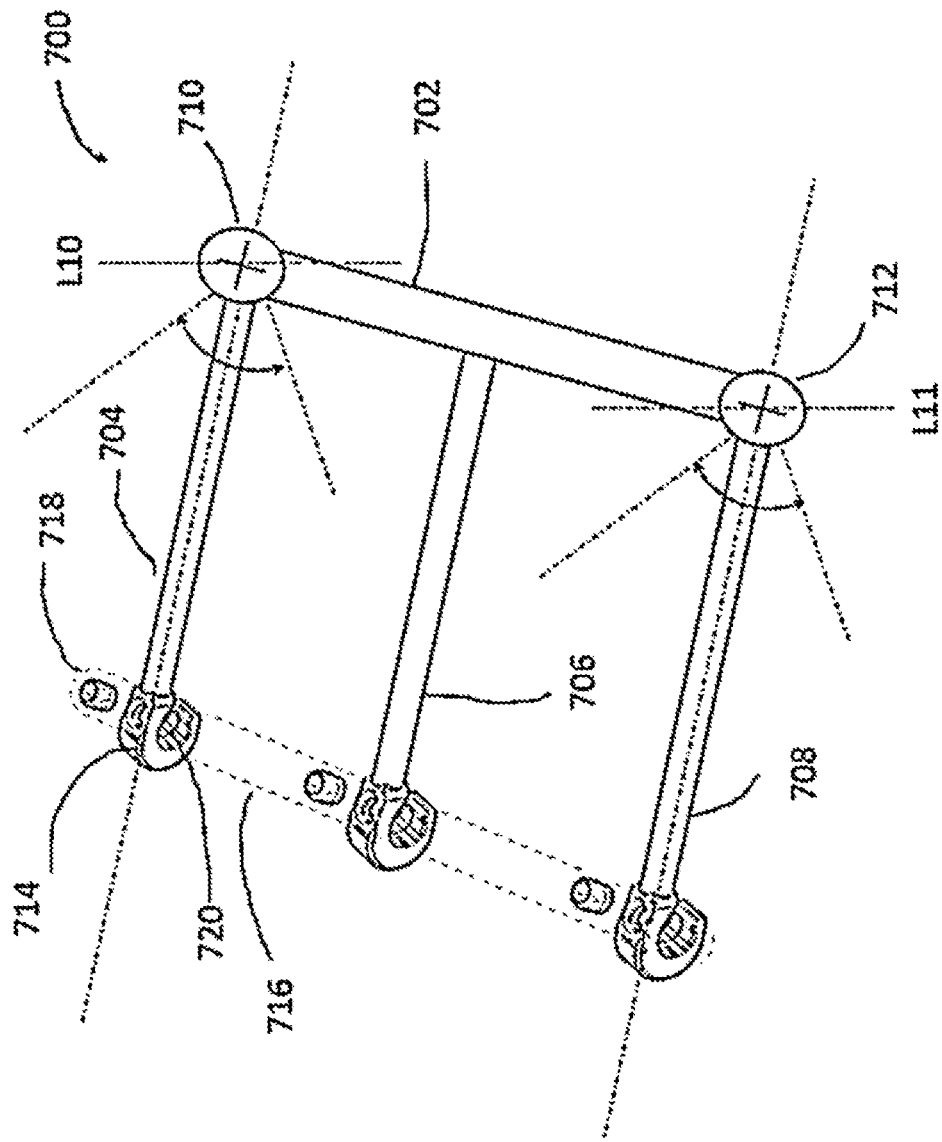
FIG. 11 is a perspective view of a spinal rod reinforcer according to one embodiment of the present invention.

FIG. 11 is a perspective view of a spinal rod reinforcer 700 according to a first embodiment of the present invention. Spinal rod reinforcer 700 includes a connector rod 702 with three attached arms. A first arm 704 is connected to one end of connector rod 702 with an adjustable screw 710. Adjustable screw 710 allows first arm 704 to be rotated about a longitudinal axis L10 and locked into position upon tightening. An opposite end of first arm 704 has a coupling mechanism 714 with a channel 720 adapted to connect to a spinal rod 716. A set screw 718 secures coupling mechanism 714 to spinal rod 716. In this embodiment, connector rod 702 is at least 30 mm long, and the width (length) of the three attached arms may range from 10 mm to 100 mm. Thickness (diameter) of connector rod 702 and each arm may range from 3.5 mm to 6.35 mm.

Connector 702 also has a second fixed arm 706 including a similar coupling mechanism 714 to connect with spinal rod 716. Finally, connector 702 includes a third arm 708 substantially similar to first arm 704. In this embodiment, all three arms are of equal length and connect to a spinal rod 716 running parallel to connector rod 702. In other embodiments, however, the number of arms may vary and the arm lengths of different arms may also vary to connect with spinal rods that are not parallel to the connector rod. Likewise, it is contemplated to allow for arm 706 to rotate like arms 704 and 708.

Figure 12:
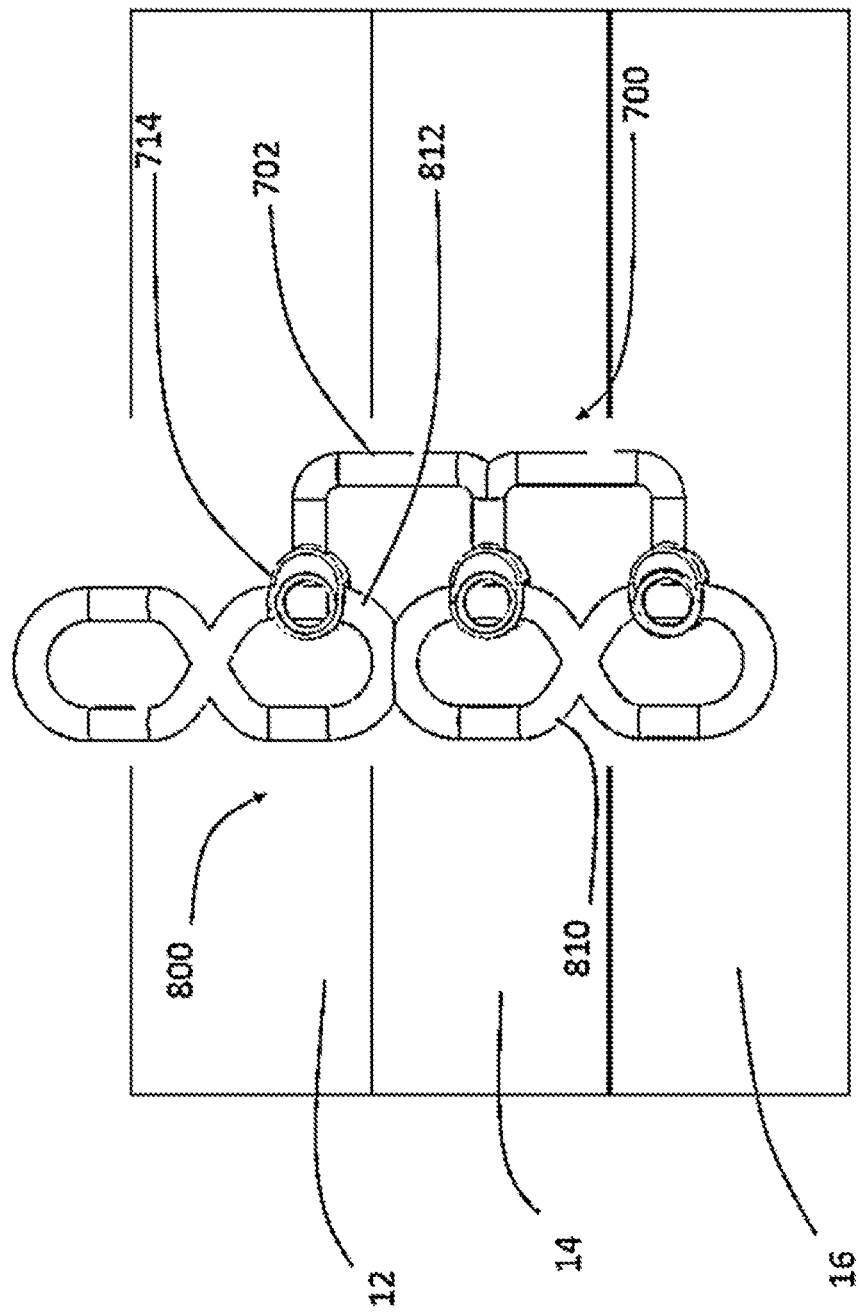
FIG. 12 is a top view of the spinal rod reinforcer of FIG. 11 connected to a spinal rod loop.

FIG. 12 shows a top view of spinal rod reinforcer 700 of FIG. 11 connected to a spinal rod loop 800 having three elliptical-shaped members. Spinal rod loop 800 connects a first vertebra 12, a second vertebra 14, and a third vertebra 16. Pedicle screws 120, 122, and 124 are attached to the first, second and the third elliptical-shaped members respectively. All three pedicle screws are attached to medial side 810 of each elliptical-shaped members of spinal rod loop 800 in this embodiment. In other embodiments, pedicle screws can be connected to different sides and in different arrangements across spinal rod loop 800, as illustrated in FIGS. 3A-C.

The three coupling mechanisms of spinal rod reinforcer 700 are attached to lateral side 812 of each elliptical-shaped member. In other embodiments, the coupling mechanisms may be attached to other sides of the elliptical-shaped members. Adjustable screws 710 and 712 allow the first and second arm respectively of spinal rod reinforcer 700 to be readily manipulated and connected to a spinal rod.

As illustrated in this figure, spinal rod reinforcer 700 can be attached to reinforce an existing spinal rod loop 800 without requiring any bone anchoring insertions, whereas attaching a second spinal rod to provide reinforcement will require at least two or more bone anchoring insertions. This is made possible because the multiple sides of spinal rod loop 800 provide rigidity to take on additional loading, and also provide multiple connection points to successfully couple a spinal rod with a suitably adapted spinal rod reinforcer 700. It is also contemplated to utilize reinforce in connection with a standard straight spinal rod to provide additional stability. In this embodiment, the length of the spinal rod loop and reinforcer may range from 45 mm to 860 mm. The combined width, i.e., from medial side 810 of spinal rod loop 800 to connector 702 may vary from 20 mm to 120 mm. The length of spinal rod reinforcer may range from 30 mm to 70 mm, with a thickness (diameter) of 3.5 mm to 6.5 mm.

In a method according to a further aspect of the present invention, spinal rod reinforcer 700 is used to reinforce spinal rod loop 800 without requiring additional pedicle screws. Spinal rod loop 800 is connected to first, second, and third vertebra 12, 14, 16, in a procedure like that described in paragraph [0029]. Spinal rod reinforcer 700 is then attached by connecting three coupling mechanisms 714, one to each elliptical-shaped member of spinal rod loop 800. Thus, spinal rod reinforcement to an existing spinal rod is provided without the addition of bone penetrating connections. Of course, reinforce can be utilized with many different types of spinal rod constructs, including, but not limited to, any of those disclosed herein.

Referring now to FIG. 13A, there is shown a spinal rod reinforcer 900 according to another embodiment of the present invention. Spinal rod reinforcer 900 is a monolithic structure with a central portion 902 and two arms 905 that can be attached to spinal rod(s) 904 by connectors 914. As used herein, the term "monolithic" is intended to mean comprising a substantially single body which, in some embodiments, may be formed, composed or created spinal rod reinforcers without joints or seams and comprising substantially, but not necessarily rigid, uniform whole. Spinal rod reinforcer 902 is pre-bent to align and connect with existing spinal rod 904 to conform to pedicle screw insertion locations and the required rod placement on the spine. Thereby, a surgeon may readily perform a quad rod technique by placing spinal rod reinforcer 902 adjacent to an existing spinal rod (revision procedure) or a newly implanted spinal rod and attaching it with connectors 914. Pedicle screws 912 can be used to fix central portion 902 at suitable locations along the vertebral body (not shown).

Revision procedures are necessary when the spinal rod construct begins to fail before the vertebral bodies fuse together. Replacing a failing spinal rod with a stronger rod construct, i.e., a thicker spinal rod, is generally not possible because the spinal fixation construct may become more prominent and may require new pedicle screws to accommodate the thicker spinal rod. Instead, surgeons may perform a quad rod technique whereby a second spinal rod is placed adjacent to and attached to an existing spinal rod. However, the quad rod procedure is time and effort-intensive requiring a surgeon, inter alia, to select a suitable second spinal rod, size the second spinal rod to match the existing rod, positioning and attaching the second spinal rod to the existing rod with rod connectors. Furthermore, the reinforcing spinal rod, i.e., the second spinal rod, must be suitably bent intra-operatively to configure the shape of the second spinal rod to the implant location. Excessive or improper bending may lead to weakening the second spinal rod and comprise the spinal fixation assembly. The spinal rod reinforcers of the present invention may be provided in a kit having multiple spinal rod reinforcers in various pre-bent configurations and sizes to allow a surgeon to select a suitable reinforcer for specific patient needs. Therefore, a surgeon may readily perform a quad rod procedure by selecting a suitable spinal rod reinforcer to match patient-specific needs pre-operatively or intra-operatively, and attaching the same to an existing spinal rod with connectors 914. While the spinal rod reinforcers described in this embodiment are pre-bent and configured to be used without any additional bending, other spinal reinforcers may allow for minor shape changes to further tailor them to patient-specific needs.

FIG. 13B shows a perspective view of another embodiment of a spinal rod reinforcer 1000. Spinal rod reinforcer 1000 is similar to spinal rod reinforcer 900, and therefore like elements are referred to with similar reference numerals within the 1000-series. For instance, spinal rod reinforcer 1000 includes a central portion 1002 and arms 1005. However, spinal rod reinforcer 1000 is generally C-shaped. Arms 1005 of spinal rod reinforcer 1000 sweep into central portion 1002 providing a larger transition area between the arms and the central portion and consequently reducing stress risers in the transition areas. The improved rigidity and stress distribution properties allow spinal rod 1000 to be implanted in confined implant locations or other quad rod procedures requiring increased rod strengths. As more fully explained above, a spinal rod reinforcer kit having multiple spinal rod reinforcers 1000 in various configurations and shapes may be provided to allow a surgeon to make patient-specific selections. After selecting a suitable patient-specific spinal rod reinforcer 1000, the spinal rod reinforcer can be attached to spinal rod 1004 with connectors 1114. Central portion 1002 provides multiple locations to fix pedicle screws 1110, 1112 to attach spinal rod reinforcer 1000 to a vertebral body (not shown). While two arms are shown in the preceding embodiments of spinal rod reinforcers 900, 1000, other embodiments may have only a single arm or multiple arms connecting the central portion and the spinal rod.

FIGS. 14A and 14B show a spinal rod connector 1100 according to one embodiment of the present invention. Spinal rod connector 1100 is a monolithic structure with a main body 1106 and a reinforcer portion having a reinforcer component 1118 substantially parallel to main body 1106. Two arms 1116 connect main body 1106 to reinforcer component 1118. Arms 1116 transfer and distribute stress from main body 1106 to reinforcer component 1118 thereby strengthening spinal rod connector 1100. Main body 1106 has a first opening 1108 at a proximal end and a second opening 1110 at a distal end. Openings 1108 and 1110 are configured to receive a first spinal rod 1102 and a second spinal rod 1104 respectively as best shown by directional arrows 1120 and 1122 in FIG. 14A. Set screws 1112 and 1114 can then be secured to holes 1124 and 1126 respectively to secure first spinal rod 1102 and second spinal rod 1114 to spinal rod connector 1100 as best shown in FIG. 14B. Other embodiments may have locking pins, press-fitting, snap fitting, or other means to securely engage spinal rods with the spinal rod connector. A depth D1 defining the length of openings 1108 and 1110 can be varied to adjust the rigidity of spinal rod connector 1106 and/or allow for adjusting spinal rod placement relative to the spinal rod connector. For example, increasing the length D1 of openings will allow greater flexibility in spinal rod placement relative to the spinal rod connector but may reduce the rigidity of the spinal rod connector because of the loss of main body material. Alternatively, a single opening may extend through main body 1106 in other embodiments wherein main body 1106 functions as a sleeve with an open interior passage.

Spinal rod connector 1110 can be used in pedicle subtraction osteotomy or corpectomy procedures wherein a surgeon can attach a first and a second spinal rod with spinal rod connector 1110 by placing the spinal rod connector over the pedicle subtraction osteotomy or corpectomy site. As more fully discussed above, a suitable spinal rod connector may be selected to provide adequate rigidity and proper placement of spinal rods relative to the spinal rod connector based on patient-specific needs. A spinal rod connector kit with multiple spinal rod connectors having different sizes and pre-bent shapes to match spine curvatures can be provided to allow a surgeon to readily select the appropriate spinal rod connector. Spinal rod connectors may also be bent by the surgeon either pre-operatively or intra-operatively to customize spinal rod connectors to patient-specific needs. Spinal rod connectors can also be used in pediatric patients whereby a surgeon can adjust the relative position of spinal rod connector 1110 with spinal rods to account for the patient's growth. Similarly, spinal rod connector may also be used in revision procedures to strengthen and connect existing spinal rods or an existing spinal rod with a new spinal rod. While a spinal rod connector with a reinforcer component is shown in FIGS. 14A and 14B, other embodiments may have spinal rod connectors without a reinforcer component thereby reducing their medial-lateral footprint and allowing them to be used in constricted surgical sites. In other embodiments, the reinforcer component may be a separate construct that can be attached to the spinal rod connector. While a reinforcer component with two arms are shown in FIGS. 14A and 14B, other embodiments may have only a single arm or multiple arms connecting the main body to the reinforcer component.

While in the all the embodiments disclosed above, the spinal fixation assembly components comprise of rods, other embodiments may be made of plates or other suitable elements. Spinal rod fixation components of the present disclosure may be made of a metal, polymers such as polyetheretherketone ("PEEK"), carbon fiber reinforced PEEK, or other suitable material such as ceramic, titanium ally, cobalt chrome, etc., that is biocompatible and possess sufficient strength to resist damage from the compressive forces associated with attaching of conventional bone screws to spinal rods. A combination of different material and/or a combination of flexible and reinforcing components to make spinal rod fixation components may also be used as described in U.S. Pat. Pub. No. 2015/0216569, the disclosure of which is hereby incorporated by reference herein. Spinal rod fixation components of the present invention may be manufactured by machining, casting, forging, additive manufacturing or other suitable methods. Spinal rod fixations elements disclosed herein may have a circular, rectangular, triangular, I-beam or any other suitable cross-section, or any combination thereof.

It is also to be understood that while dimensional ranges for various embodiments are discussed above, the dimensions of embodiments according to the present invention may vary widely depending upon the particular application for which the embodiments are to be utilized. Thus, embodiments that fall outside of the specific ranges given herein are clearly contemplated, and the particular dimensions given here should be taken as merely exemplary.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A spinal rod assembly comprising:
   a spinal rod,
   a monolithic spinal rod reinforcer having two or more arms extending transverse to a main body, each arm having a coupling mechanism with a coupling channel adapted to receive the spinal rod,
   a first pedicle screw having a first channel;
   a second pedicle screw having a second channel, and
   a third pedicle screw having a third channel configured to attach the main body of the spinal rod reinforcer to a vertebral body,
   wherein the first pedicle screw and the second pedicle screw are configured to attach the spinal rod to the vertebral body, and the coupling mechanisms of the spinal rod reinforcer are attached to the spinal rod such that the spinal rod is received in the first and second channels and the coupling channels.

2. The spinal rod assembly of claim 1, wherein the two or more arms are attached to opposite ends of a central portion of the main body such that the spinal rod reinforcer is substantially C-shaped.

3. The spinal rod assembly of claim 2, wherein the central portion is substantially parallel to the spinal rod.

4. The spinal rod assembly of claim 1, wherein the spinal rod is a loop having one or more sides such that the first and second pedicle screws attach to one loop side.

5. The spinal rod assembly of claim 1, wherein the two or more arms include a first arm and a second arm extending transverse to the main body, the first arm having a first coupling mechanism with a first coupling channel adapted to receive the spinal rod, the second arm having a second coupling mechanism with a second coupling channel adapted to receive the spinal rod, wherein when the coupling mechanisms of the spinal rod reinforcer are attached to the spinal rod the spinal rod is received in the first and second channels and the first and second coupling channels.

6. The spinal rod assembly of claim 5, further including a third arm extending transverse to the main body, the third arm having a third coupling mechanism with a third coupling channel adapted to receive the spinal rod, wherein when the coupling mechanisms of the spinal rod reinforcer are attached to the spinal rod the spinal rod is received in the first and second channels and the first, second and third coupling channels.

7. The spinal rod assembly of claim 5, wherein the first and second arms extend substantially perpendicular to the main body.

8. The spinal rod assembly of claim 7, wherein a length of the first arm defined by the extension of the first arm from the main body is substantially the same as a length of the second arm defined by the extension of the second arm from the main body.

9. The spinal rod assembly of claim 1, wherein each coupling mechanism includes a fastener to secure the spinal rod to the respective coupling channel.

10. The spinal rod assembly of claim 9, wherein the fastener is set screw.

* * * * *